United States Patent [19]
Landegren

[11] Patent Number: 5,618,701
[45] Date of Patent: Apr. 8, 1997

[54] METHOD OF PROCESSING NUCLEIC ACID SAMPLES

[75] Inventor: Ulf Landegren, Upsala, Sweden

[73] Assignee: Pharmacia Biotech AB, Upsala, Sweden

[21] Appl. No.: 432,115

[22] PCT Filed: Nov. 5, 1993

[86] PCT No.: PCT/SE93/00929

§ 371 Date: May 5, 1995

§ 102(e) Date: May 5, 1995

[87] PCT Pub. No.: WO94/11529

PCT Pub. Date: May 26, 1994

[30] Foreign Application Priority Data

Nov. 6, 1992 [SE] Sweden ................... 9203320

[51] Int. Cl.$^6$ ........................................ C12P 19/34
[52] U.S. Cl. .................. 435/91.1; 435/91.2; 422/56; 422/99; 422/292; 935/76; 935/79
[58] Field of Search ................. 435/91.1, 91.2; 422/56, 99, 292; 536/23.1, 24.3, 25.42; 935/76, 79

[56] References Cited

U.S. PATENT DOCUMENTS

| | | | |
|---|---|---|---|
| 4,891,321 | 1/1990 | Hubscher | 422/99 |
| 5,244,788 | 9/1993 | Hubscher | 422/56 |
| 5,436,129 | 7/1995 | Stapleton | 435/91.1 |

FOREIGN PATENT DOCUMENTS

| | | |
|---|---|---|
| 102661 | 3/1984 | European Pat. Off. . |
| 184056 | 6/1986 | European Pat. Off. . |
| 279506 | 6/1990 | German Dem. Rep. . |
| 0259628 | 8/1988 | Germany ................... 536/25.42 |

OTHER PUBLICATIONS

English Abstract of East German Patent DD 279 506A.
JP Abstract No. 1-108999.

*Primary Examiner*—Paul B. Prebilic
*Attorney, Agent, or Firm*—Birch, Stewart, Kolasch & Birch, LLP

[57] ABSTRACT

A method of processing nucleic acid samples for analysis comprises the use of one or more manifolds (10) with a plurality of individual solid phase members (11) adapted for cooperation with a corresponding set or sets of receptacles (13; 15; 17). A nucleic acid species in a sample is bound to each solid phase member (11) by introducing the solid phase members into a receptacle or set of receptacles (13; 15; 17) which contain the sample or samples. Optionally, the bound nucleic acid species may be processed in a second set or sets of receptacles, and reaction products therein may be bound to the solid phase members (11) of a second manifold or manifolds. The solid phase members (11) of the first or second manifolds are then introduced into the sample receptacle or receptacles of an analyser for analyzing the nucleic acid species or reaction products, wherein nucleic acid species or reaction products are released from the solid phase members (11).

12 Claims, 1 Drawing Sheet

METHOD OF PROCESSING NUCLEIC ACID SAMPLES

FIELD OF THE PRESENT INVENTION

The present invention relates to the analysis of nucleic acids, and more particularly to a method of processing nucleic acid samples for or as a part of analytical procedures.

BACKGROUND OF THE INVENTION

Laboratory processes involving nucleic acid sequences are nowadays very common and often performed as a matter of routine. Such processes include inter alia hybridizing and enzymatic reactions.

A common type of such processes is amplification reactions, such as the polymerase chain reaction, or abbreviated PCR. As is well-known, the PCR technique provides for the highly specific amplification of unique DNA segments defined by two surrounding primer sequences. PCR thereby offers a convenient way of obtaining sufficient quantities of DNA for inter alia nucleotide sequencing purposes. One major application of PCR is for diagnostic purposes. For a description of PCR it may, for example, be referred to White, T. et al., Trends in Genetics, 5, 179 (1989).

Extensively used solid supports in the context of molecular-genetic reactions have so far been paramagnetic beads due to the large total area provided thereby and their simplified handling and processing. Thus, for example, such magnetic beads having streptavidin immobilized thereto are commercially available.

However, the simultaneous processing of large sets of samples through sequential reaction steps using e.g. magnetic beads as a solid phase is technically demanding and involves a substantial risk of contamination between reactions. This is, of course, particularly undesired in amplification contexts, such as PCR, where the multiplication of contaminating sequences may result.

DD-A-279 506 discloses the use of a multipronged device for DNA-sequencing on a solid phase by chemical degradation (Maxam-Gilbert method). The device has a set of rods, each with immobilization primers attached, which rods are designed to fit into a set of reaction vessels. The labelled DNA fragments to be sequenced are immobilized to the rods by dipping them into respective vessels containing the DNA fragments. The further processing of the immobilized DNA fragments is conducted by dipping the rods into vessels containing corresponding reagents and solution, and the contents of the respective vessels containing DNA fragments degraded by the respective base specific reagents are lyophilized and then subjected to gel electrophoresis.

It is readily seen that the use of a multipronged device as suggested by Rosentahl et al., supra, obviates several of the problems related to the use of separate solid phase elements, like paramagnetic beads or microtiter wells, for example. A problem of this "patrix-matrix" type approach, however, which is likely to have limited its application, has been to provide for sufficient binding capacities on the individual prongs.

It may be mentioned in this context that a similar "patrix-matrix" strategy, permitting sets of solid supports (patrices) to be coordinately moved between corresponding sets of reaction wells (matrices), has previously been applied in peptide synthesis. Also, a type of multipronged solid support permitting the simultaneous processing of multiple samples is commercially available for immunoassay applications.

Thus, while a nucleic acid sample procedure using a multipronged device as described above may simplify the procedure significantly and reduce the risk of mix-up and contamination to a substantial degree, there still remains, however, the relatively cumbersome step of releasing the reaction products from the solid support and transferring them to the analyzer apparatus in question.

SUMMARY OF THE PRESENT INVENTION

In accordance with the present invention there is therefore suggested a further improvement in the use of multipronged solid supports in the analysis of nucleic acid samples, which improvement consists in adapting the multipronged device such that the release from the solid supports of reaction products to be analyzed may be conducted directly into the analyzer in question, thereby avoiding inter alia laborious pipetting procedures for the sample application. Not less importantly, this makes it possible to use a single solid phase set or a series of solid phase sets for all processing of the nucleic acid samples from the adsorption thereof to the solid supports to the desorption thereof, or of reaction products, on the supports to the analyzer, such as e.g. an electrophoretic gel. It is readily seen that such a format will considerably simplify the parallel and serial transfer of multiple samples through sequential reaction steps from the isolation of a target molecule from a complex sample up to the final analyzing step while substantially decreasing the risk of mix-ups and contamination among samples.

The present invention thus provides a method of processing nucleic acid (DNA or RNA) samples for analysis, comprising the steps of providing one or more manifolds having a plurality of individual solid phase members adapted for cooperation with a corresponding set or sets of receptacles, binding a nucleic acid species from a sample to each solid phase member of a first manifold or manifold set by introducing the solid phase members into a first receptacle or set of receptacles containing said sample or samples, optionally processing each nucleic acid species while it is bound to the solid phase member by introducing the solid phase members into a second set or sets of receptacles, optionally introducing the solid phase members of a second manifold or manifold set into the second receptacles to immobilize one or more species generated in the receptacles to the solid phase members, and releasing nucleic acid species or reaction products from the solid phase members of the manifold or manifolds to an analyzer for analyzing the nucleic acid species or reaction products by introducing the solid phase members into a sample receptacle or receptacles of the analyzer, which receptacle or receptacles provide for the necessary environment for said release.

The term "analyzer" as used herein is to be interpreted in a broad sense. Thus, the analyzer need not be an actual analytical instrument but may, for example, be a set of microtiter wells in which a colour reaction is detected, such as visually.

The necessary environment and conditions for the release or desorption of the material to be analyzed from the manifold solid phase members into the analyzer varies depending on the particular species to be released and the particular analyzer. For example, in the case of a DNA-sequence analysis comprising gel electrophoresis, the manifold is designed such that the solid phase members thereof may be conveniently introduced into the sample wells of the electrophoretic gel plate, in which wells desorption of the synthesized nucleic acid strands may be effected by means of, for example, a denaturant, such as formamide, heat and/or a denaturing pH, e.g. alkali.

The solid phase members may be provided in various ways within the scope of the present invention. In one embodiment they are prongs or pins extending from the surface of a plate member. Such a system may for instance have a number of e.g. 96 prongs adapted to fit into the wells of a 96 well microtiter plate which may be of conventional type. In another embodiment the manifold is a comb-like element having, for example, four, eight or more prongs. Suitably, the manifolds are designed such that two or more manifolds may be interconnected and stacked together one behind the other to form a manifold assembly exhibiting several rows of prongs, and/or interconnected in a side-by-side relationship. In still another embodiment the solid phase members are defined surface areas of a first plate means adapted to cooperate with respective areas (e.g. recesses) in a second plate means to define a plurality of reaction volumes therewith.

To permit the binding of said nucleic acid species to the solid phase members, there is immobilized to the solid phase surface a molecule or group capable of interacting with the nucleic acid species per se or with a functional group or molecule incorporated into the nucleic acid species.

In the former case, the solid phase surface may support an oligonucleotide, e.g. covalently bound to the solid phase, which oligonucleotide is capable of hybridizing with or ligating to the nucleic acid species.

In the latter case, the functional group incorporated into the nucleic acid may be one member of a specific binding pair, the other member being supported by the solid phase. Exemplary of such binding pairs are biotin—avidin, biotin—streptavidin, cystein—thiol groups, antigen—antibody, lectin—sugar. A particularly useful binding pair in the present context is biotin—avidin (or streptavidin). The use of such a specific binding pair for immobilizing DNA to a solid phase is described in e.g. WO 89/099282, which discloses the immobilization for sequencing purposes of a single stranded DNA template on an insoluble carrier by selective incorporation of a functional group into one of the DNA strands of a plasmid or phage vector, followed by directed immobilization of this vector to a solid support via the functional group, and subsequent selective elution of the non-bonded DNA-strand with suitable conditions.

For the purposes of the invention, the solid phase members may advantageously be provided with a substantially expanded surface area, permitting increased surface loading, by coating the surfaces with porous particles. A suitable coating method involving the attachment of particles to the surface without the use of adhesive is described in our concurrently filed International (PCT) patent application entitled "A method of surface modification" (based on Swedish patent application No. 9203319-0), the disclosure of which is incorporated by reference herein. Such particle coating of the solid phase members will readily provide for the achievement of sufficient binding capacities for the intended purposes.

The above described "fishing" approach for the immobilization of target molecules to the solid phase members will permit simple and efficient purification of nucleic acid molecules and/or enrichment for specific target molecules from even very complex or crude sample solutions, eliminating special purification steps.

In a general embodiment, the method of the present invention may comprise the following steps: (i) sampling; (ii) selection and optional amplification of the desired nucleic acid material; (iii) optional processing of the nucleic acid material; and (iv) application to the analytical instrument (analyzer), such as e.g. an electrophoretic gel; with appropriate washes therebetween.

The selection is typically performed such that one strand of a nucleic acid material of interest, e.g. DNA, either has or is provided with a unique chemical group chosen to selectively and strongly bind to another molecule which can be immobilized to the solid phase. Exemplary of such pairs of interacting molecules or groups, i.e. specific binding pairs, are as already mentioned above biotin—streptavidin, and two hybridizing or ligating single stranded DNA molecules. The interaction between the solid phase and the target molecule may thus be of covalent as well as non-covalent type.

The unique chemical group may, for example, be introduced by making an oligonucleotide (primer) complementary to one of the strands of the nucleic acid material of interest and provided with the unique chemical group at the 5'-end. This primer may then hybridize to its complementary strand and subsequently be extended in the presence of the four nucleotides (dNTP's) and a DNA dependent polymerase. If such a primer is combined with a second primer, simultaneous amplification and selection may be obtained, e.g. by means of PCR, as is per se known in the art.

The nucleic acid material thus end-labelled with the unique chemical group may then be selectively bound to the solid phase members of the manifold, the solid phase members each supporting a molecule or group capable of interacting with the unique chemical group of the above-mentioned primer, i.e. the other member of the specific binding pair. By this process, selection as well as enrichment and the possibility of efficient washing is obtained.

In some cases a succession of manifolds may be used. For instance, a first manifold (or set) may be utilized for fishing a target molecule from a complex sample. The immobilized molecule may then be processed to generate one or more desired species in the reaction solution. This or these species may then be immobilized to a second manifold (or set) to be further processed as described above. Optionally, this procedure may be repeated one or more times with different manifolds (or sets) before one or more desired species are eventually analyzed.

The manifold may as suggested above, for example, be in the form of a comb-like means, the prongs or teeth of which represent said solid phase members and have been provided with suitable surface characteristics (hydrophilicity, available surface area, etc) as well as with the desired interacting group as described above.

The nucleic acid material bound as above may then, if desired, be subjected to various chemical environments by introducing the solid phase members, or prongs, into wells with suitable contents. Since the individual prongs are integral with a common carrier, any desired number of individual prongs may each be moved and individually processed by being introduced into respective wells. Typically, this processing consists in synthesizing a complementary molecule on each immobilized nucleic acid material (template). These complementary molecules may then be desorbed from the respective prongs by subjecting the latter to a suitable environment in direct connection with the following analysis to be performed on these released complementary molecules. In, for example, the case of a gel electrophoresis, the manifold, such as the mentioned comb-like means, is designed such that the different solid phase members, or prongs, will fit into the wells of the electrophoretic gel plate for the desorption process to take place therein.

BRIEF DESCRIPTION OF THE DRAWINGS

Embodiments of the manifold and receptacle sets therefore will now be described with reference to the acccompanying drawings, wherein.

DETAILED DESCRIPTION OF THE INVENTION

Figure 1:
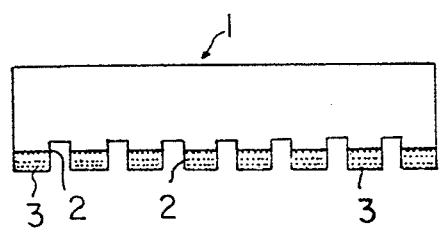
FIG. 1 is a front view of a comb-like manifold.

The comb-like manifold schematically illustrated in FIG. 1 and generally designated by reference numeral 1 has eight prongs or teeth 2. The shape of the teeth 2 and their spacing are adapted to the sample wells of an electrophoretic apparatus as will be described in more detail below. In the figure, the teeth 2 have been derivatized, indicated by shading 3, e.g. coated with avidin-conjugated particles as described in our aforementioned copending International (PCT) patent application and in Example 1 below.

The manifold 1 is designed to cooperate with corresponding well sets, two different embodiments of which are shown in FIGS. 2, 3 and 4, 5, respectively. The well set of FIGS. 2 and 3 has two elongate wells 4, each capable of receiving four manifold teeth 2. In the illustrated case, the wells 4 are partially filled with reagent solution 5. The well set embodiment illustrated in FIGS. 4 and 5, on the other hand, has eight individual wells 6, each well 6 being adapted to receive a single manifold tooth 2 and here also shown as partially filled with reagent solution 7.

Figure 6:
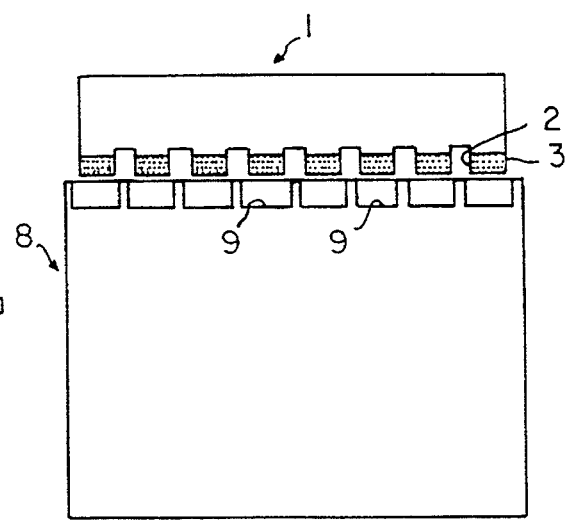
FIG. 6 is a schematic front view showing the manifold of FIG. 1 aligned with the sample wells of an analytical apparatus.

As mentioned above, manifold 1 is adapted to cooperate with the sample wells of an analytical apparatus. This is schematically illustrated in FIG. 6, where manifold 1 is placed above an electrophoretic apparatus, generally designated by reference numeral 8, with the teeth 2 aligned with and capable of being received in respective sample wells 9 of the electrophoretic apparatus.

DNA sequencing according to the chain termination or dideoxy method using the manifold and well sets described above may be conducted as follows:

Manifold 1 is provided with streptavidin immobilized to the teeth 2 thereof as indicated at 3 in FIG. 1. First, PCR on a desired DNA sequence is performed in per se conventional manner in each elongate well 4 of the well strip of FIGS. 2 and 3, using one biotin-labelled primer and one non-labelled primer. The streptavidin-coated teeth 2 of manifold 1 are then introduced into the reaction mixtures 5 in the wells 4 to bind the respective biotin-labelled PCR reaction products thereto, i.e. in the illustrated case a first PCR reaction product to one set of four adjacent teeth and a second PCR reaction product to the other set of four teeth. One strand of each double-stranded DNA fragment is then melted off by subjecting the teeth to denaturing conditions, e.g. heat and/or alkali treatment. If desired, the denaturing to single-stranded DNA may, however, be performed already in the PCR reaction mixture after completed reaction prior to the immobilization to the solid phase.

Figure 2:
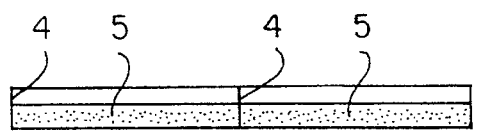
FIG. 2 is a schematic sectional view of a well strip with two elongate wells.
Figure 3:
FIG. 3 is a schematic top view of the well strip in FIG. 2.

After removal of the teeth from the two wells 4 and removal of the non-bound DNA strands and other reaction components in a quick wash step in another set of wells, or by other means, the manifold teeth 2 are introduced into the wells 4 of a second well strip of the type shown in FIGS. 2 and 3 containing a reaction solution 5 for hybridizing a labelled primer (e.g. a coloured or fluorescent tag) to the single stranded DNA fragments or templates bound to the manifold teeth 2. Alternatively, dNTP's or ddNTP's used in the subsequent extension reaction steps may be labelled instead of the primers.

Figure 4:
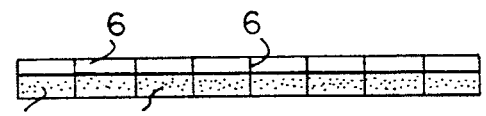
FIG. 4 is a schematic sectional view of a well strip with eight wells.
Figure 5:
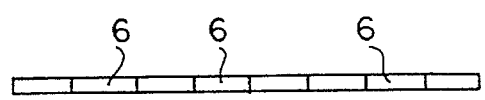
FIG. 5 is a schematic top view of the well strip in FIG. 4.

The manifold 1 is then removed from the well strip, and after a quick wash the teeth 2 thereof are introduced into the eight individual wells 6 of the well strip shown in FIGS. 4 and 5, each set of four wells 6 containing sequence reaction mixtures 7 with a respective dideoxynucleotide (ddNTP) in each well to permit nucleotide polymerizations on the solid phase-bound templates in per se known manner.

After washing of the manifold teeth 2, manifold 1 is now transferred to and aligned with the electrophoretic apparatus 8 as shown in FIG. 6, and the manifold teeth 2 are introduced into the sample wells 9 of the electrophoretic apparatus 8. The sample wells 8 contain a suitable agent solution, e.g. formamide, for effecting desorption of the mixture of dideoxy terminated extension products from the templates carried by each manifold teeth 2. After desorption for a few minutes, the manifold 1 is lifted out from the wells 9, and the electrophoretic process is started.

Figures 7A, 7B, 7C:
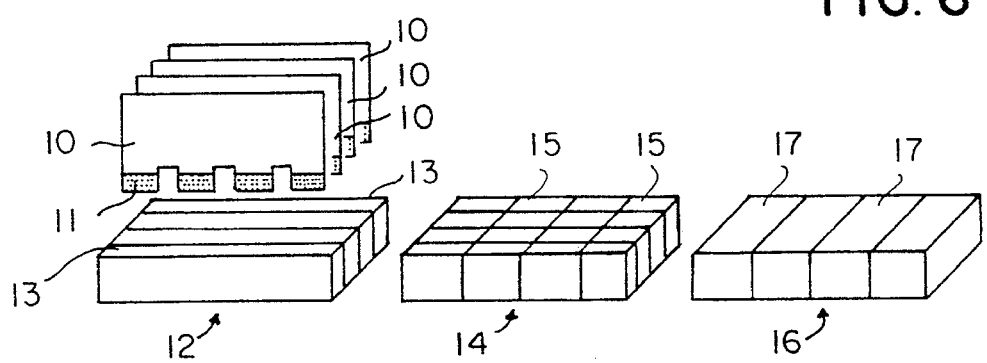
FIGS. 7A–7C are a schematic perspective view of a set of four manifolds and three different sets of wells.

FIG. 7 illustrates a set of several, here four, manifolds 10, each having four teeth 11. Manifolds 10 are designed to permit being stacked together by suitable means (not shown), without the teeth 11 of adjacent manifolds contacting each other, such that all four manifolds may be handled as a single unit. In FIG. 7, the manifold set is placed above and aligned with a corresponding set 12 of elongate wells 13, each well 13 being adapted for receiving all four teeth of one manifold 10. There is also shown a second well set 14 having respective wells 15 for each manifold tooth 11. Finally, a third well set 16 is shown, having four elongate wells 17 arranged transversely to the wells 13 of well set 12 to each receive a respective tooth row (consisting of one tooth 11 from each manifold 10) of the stacked manifold set.

To perform the sequencing procedure described above with a manifold/well set shown in FIG. 7, desired DNA fragments are immobilized to the teeth 11 of manifold 10 by dipping the teeth into the respective wells 13 containing corresponding PCR amplification mixtures. The sequencing reactions may then be performed either in the wells 15 of well set 14 (correspondingly as in wells 6 of the well set of FIGS. 4 and 5 described above), or in the wells 17 of well set 16. In the latter case, each one of the four sequencing reactions (A, C, T and G reactions) is carried out simultaneously on a respective row of stacked teeth 11 of the manifold assembly. It is readily seen that this embodiment significantly reduces the necessary number of operations for dispensing reaction solutions to the different wells.

Rather than using a single labelled primer as described above, it is also possible to use either four differently labelled primers or four differently labelled dideoxy terminators as is per se known in the art. In the case of labelled primers, the four sequencing reactions are run on four separate teeth, and the reaction mixtures are then combined to be read on e.g. an automatic fluorescent reader. In this case individual wells will, of course, have to be used for each manifold tooth for hybridizing the different primers to the manifold-immobilized DNA templates. In the case of labelled terminators on the other hand, all sequencing reactions may be performed on a single manifold tooth.

Advantageously, the manifolds and well sets may be provided in a kit form, which preferably has the necessary reagent components present in a dried state in the wells and/or on the solid phase members. For a more detailed description of dried state reaction mixtures, it may be referred to, for example, EP-A-298 669, EP-A-383 569 and U.S. Pat. No. 4,891,319 (the disclosures of which are incorporated by reference herein).

In the following the invention is illustrated by non-limiting examples.

EXAMPLE 1

A. Conjugation of avidin to Sepharose® particles

SEPHAROSE particles, chemically cross-linked agarose beads, HITRAP, a disposable chromatographic column; NHS-activated SEPHAROSE HP, SEPHAROSE activated with N-hydroxy succinimide, HP means high performance and is indicative of particle size, Pharmacia LKB Biotechnology AB, Uppsala Sweden) corresponding to 6.0 ml of sedimented material, were carefully washed with ice cold 1 mM HCl (3×10 ml) on a sintered funnel, making sure that the SEPHAROSE surface did not at any time become dry. The particles were quickly washed with a solution of 1.0M NaCl and 0.4M $NaHCO_3$, buffered to pH 8.3, and transferred to a final volume of 5 ml of the above buffer, containing 10 mg of avidin. The suspension was incubated rotating end-over-end for one hour, filtered, and the particles were blocked in 0.1M ethanolamine buffer, pH 8.3, for 15 minutes. The avidin-conjugated SEPHAROSE particles were then washed with 0.1M acetate buffer, pH 4.0, and used immmediately or stored in 0.05M Tris-buffer, pH 7.3, with 0.02% (w/v) sodium azide.

B. Attachment of particles to a polystyrene solid support

Avidin-conjugated particles as prepared above were filtered, washed with distilled water, dried with methanol (3×5 ml), and then equilibrated with triethylamine ($Et_3N$; (3×5 ml). The solid was quickly transferred to a suitable vessel and $Et_3N$ was added to obtain a slurry of about 75% (v/v) particles. A polystyrene support, configured as a microtiter plate lid with 8 rows of 12 pin-and-ball extensions adapted to project into individual microtiter wells of a corresponding microtiter plate (F.A.S.T. system, Falcon, Oxnard, Calif., U.S.A.) was washed with ethanol for 20 minutes in an ultrasonic bath and the particles were then grafted onto the projections from the polystyrene support by two submersions in the slurry, each for 2 seconds, followed by immediate evaporation of the residual $Et_3N$ in air. After washing in deionized water, detached particles were collected and reused. Loosely bound particles were removed by a 10 minutes incubation shaking in water. The manifold was stored until use in buffer (1M NaCl, 100 mM Tris-HCl, pH 7.5, and 0.1% (v/v) Triton X 100), with the addition of 0.5% (w/v) fat-free dry milk and 0.02% sodium azide.

Testing of the binding capacity of the avidin-coated support by means of a $^{32}P$-labelled oligonucleotide, 5'-modified with biotin, indicated that each prong of the support could bind in the order of 20 pmol of biotinylated oligonucleotides.

EXAMPLE 2

The teeth of a comb-like polystyrene manifold of the type shown in FIG. 1 were coated with avidin-coupled beads up to about 5 mm from the tooth tips in the same manner as described in Example 1 above.

DNA dideoxy sequencing reactions were then performed substantially according to the standard protocol described by Hultman et al. (1989) NAR 17: 4937–4946, by first trapping and purifying the 5'-biotinylated template strand on the manifold teeth and then dipping the manifold teeth into wells containing the appropriate reaction media.

After completed sequencing reactions, the teeth of the manifold were introduced into the wells of the sequencing gel of an A.L.F.™ DNA Sequencer (Pharmacia LKB Biotechnology AB, Uppsala, Sweden), the wells containing concentrated formamide. The teeth were allowed to remain submersed in the formamide for 5 minutes at room temperature. The electrophoresis was then started and stopped after another 5 minutes when the manifold was removed. The electrophoresis was then continued and run in per se conventional manner. The sequence reading indicated that efficient desorption and gel separation of the dideoxy-terminated reaction fragments had taken place in the sample wells.

The invention is, of course, not restricted to the embodiments specifically described above and shown in the drawings, but many changes and modifications may be made without departing from the scope of the general inventive concept as defined in the following claims.

I claim:

1. A method of processing nucleic acid samples for analysis, comprising the steps of providing one or more manifolds having a plurality of individual solid phase members wherein said solid phase members extend from said one or more manifolds and are adapted for cooperation with a corresponding set or sets of receptacles;

binding a nucleic acid containing species from a sample to each solid phase member of a first manifold by introducing the solid phase members of said first manifold into a first receptacle or set of receptacles containing said sample;

optionally processing each nucleic acid containing species while it is bound to the solid phase member of said first manifold to produce nucleic acid containing reaction products by introducing the solid phase members of said first manifold into a second set or sets of receptacles;

optionally introducing the solid phase members of a second manifold into said second set or sets of receptacles to immobilize one or more nucleic acid containing reaction products generated therein to the solid phase members of said second manifold;

and releasing directly to an analyzer said nucleic acid containing species or said reaction products from the solid phase members of the first and second manifold for analysis of the nucleic acid containing species or reaction products by introducing the solid phase members into a sample receptacle or receptacles of said analyzer, which receptacle or receptacles provide for the necessary environment for said release.

2. The method according to claim 1, wherein said nucleic acid containing reaction products are extended primer sequences synthesized on DNA templates bound to the solid phase members.

3. The method according to claim 1, wherein said release is effected by treatment with a denaturant.

4. The method according to claim 3, wherein said denaturant is selected from the group consisting of formamide, heat and a denaturing pH, and combinations thereof.

5. The method according to claim 1, further comprising performing amplification reactions on templates bound to the solid phase members.

6. The method according to claim 1, wherein each said one or more manifolds is an element having a number of teeth forming said solid phase members.

7. The method according to claim 6, wherein said analyzer comprises a sequencing gel having sample wells adapted to receive said teeth.

8. The method of claim 5 wherein said amplification reaction is PCR.

9. The method of claim 6 wherein said element has four teeth.

10. The method of claim 6 wherein said element has eight teeth.

11. The method of claim 1 further comprising releasing into a solution said nucleic acid containing species or reaction products and analyzing the solution.

12. A method of processing nucleic acid samples for a diagnostic procedure comprising:

obtaining a sample containing nucleic acid;

processing said sample using the method of claim 1.

* * * * *